(12) United States Patent
Fiorini et al.

(10) Patent No.: US 12,171,414 B2
(45) Date of Patent: Dec. 24, 2024

(54) SURGICAL DEVICE FOR TRANSPERINEAL BIOPSY, IN PARTICULAR OF THE PROSTATE, FOR A MOVABLE ARM OF A ROBOT

(71) Applicant: UNIVERSITA' DEGLI STUDI DI VERONA, Verona (IT)

(72) Inventors: Paolo Fiorini, Verona (IT); Francesco Bovo, Verona (IT)

(73) Assignee: UNIVERSITA' DEGLI STUDI DI VERONA (IT)

( * ) Notice: Subject to any disclaimer, the term of this patent is extended or adjusted under 35 U.S.C. 154(b) by 685 days.

(21) Appl. No.: 17/431,639

(22) PCT Filed: Feb. 20, 2020

(86) PCT No.: PCT/IB2020/051437
§ 371 (c)(1),
(2) Date: Aug. 17, 2021

(87) PCT Pub. No.: WO2020/170195
PCT Pub. Date: Aug. 27, 2020

(65) Prior Publication Data
US 2022/0110613 A1    Apr. 14, 2022

(30) Foreign Application Priority Data
Feb. 20, 2019   (IT) .......................... 102019000002475

(51) Int. Cl.
*A61B 10/02*   (2006.01)
*A61B 8/00*    (2006.01)
(Continued)

(52) U.S. Cl.
CPC ............ *A61B 10/0241* (2013.01); *A61B 8/12* (2013.01); *A61B 8/4218* (2013.01);
(Continued)

(58) Field of Classification Search
None
See application file for complete search history.

(56) References Cited

U.S. PATENT DOCUMENTS

2005/0203413 A1   9/2005  Fichtinger et al.
2008/0004481 A1*  1/2008  Bax ................... A61B 17/3403
                                                        600/7
(Continued)

FOREIGN PATENT DOCUMENTS

JP    2016505314 A    2/2016
WO    2016044939 A1   3/2016

OTHER PUBLICATIONS

Office Action issued in counterpart Japanese Patent Application No. 2021-549157 on Nov. 10, 2023.
(Continued)

*Primary Examiner* — Jason M Ip
*Assistant Examiner* — Renee C Langhals
(74) *Attorney, Agent, or Firm* — The Belles Group, P.C.

(57) ABSTRACT

A device for transperineal biopsy with a movable arm of a robot, comprising: an ultrasound probe being mounted around a first axis; a surgical instrument with a needle, which is movable along a first trajectory; and a moving device comprising at least a first pair of arms facing one another and arranged around a first longitudinal axis of the ultrasound probe so as to move, preferably oscillate, around the axis along a second trajectory, in order to guide and support the needle at a free end of each guide arm; and a connection interface to connect the device to a movable arm of a robot and having an operating module, which comprises a plurality of actuators each to move a respective said ultrasound probe or said guide arms, and a separation module arranged on the operating module and configured to transmit the motion to the ultrasound probe or to the arms.

14 Claims, 5 Drawing Sheets

(51) Int. Cl.
*A61B 8/12* (2006.01)
*A61B 17/34* (2006.01)
*A61B 34/30* (2016.01)
*B25J 9/00* (2006.01)

(52) U.S. Cl.
CPC .......... *A61B 17/3403* (2013.01); *A61B 34/30* (2016.02); *A61B 2017/3413* (2013.01); *A61B 2034/303* (2016.02); *B25J 9/00* (2013.01)

(56) References Cited

U.S. PATENT DOCUMENTS

| | | |
|---|---|---|
| 2010/0041938 A1* | 2/2010 | Stoianovici ............ A61B 34/30 600/7 |
| 2010/0056900 A1 | 3/2010 | Whitcomb et al. |
| 2014/0039314 A1 | 2/2014 | Stoianovici et al. |
| 2015/0080907 A1* | 3/2015 | Herrell ................. A61B 1/0016 606/130 |
| 2015/0173727 A1 | 6/2015 | Lohmeier et al. |
| 2015/0366544 A1 | 12/2015 | Yap et al. |
| 2016/0151115 A1 | 6/2016 | Karguth et al. |
| 2017/0252248 A1 | 9/2017 | Plante et al. |

OTHER PUBLICATIONS

Intention to Grant issued in counterpart European Application No. 20713367.9 on Aug. 23, 2023.

* cited by examiner

SURGICAL DEVICE FOR TRANSPERINEAL BIOPSY, IN PARTICULAR OF THE PROSTATE, FOR A MOVABLE ARM OF A ROBOT

CROSS-REFERENCE TO RELATED APPLICATIONS

This patent application is a U.S. national stage application under 35 U.S.C. § 371 of PCT Application No. PCT/IB2020/051437, filed Feb. 20, 2020, which claims priority from Italian patent application no. 102019000002475 filed Feb. 20, 2019, the entire disclosure of the aforementioned priority applications are incorporated herein by reference in their entireties.

TECHNICAL FIELD

The present invention relates to a surgical device for transperineal biopsy, in particular of the prostate, for a movable arm of a robot.

PRIOR ART

It is common practice to use robots for performing minimally invasive surgical operations. In particular, a surgical robot as described for example in US2008004481, US2014039314, US2010056900 or US2015173727 carries one or more specific surgical instruments and allows a surgeon to perform complex surgical operations in a minimally invasive manner by means of the integration of a high definition 3D viewing system with an intuitive control system for controlling the surgical instruments. The surgical robot typically comprises a surgical console, a patient-side cart and a viewing trolley. In particular, the patient-side cart is provided with a plurality of anthropomorphic arms, each of which is provided with a surgical instrument.

The surgical robots of known type are compatible and usable only and exclusively with surgical devices such as, for example, devices for robotic biopsy, purposely developed to be associated with a given surgical robot. Therefore, it is not possible to use surgical devices different from those developed for a given surgical robot, thus limiting the range of surgical instruments available on the market and increasing the cost thereof.

Surgical devices are consequently very costly and cannot be used with a robot different from the one for which they have been developed.

DESCRIPTION OF THE INVENTION

The aim of the present invention is therefore to provide a surgical device for transperineal biopsy, in particular of the prostate, for a movable arm of a robot which is without the drawbacks of the state of the art, and which is easy and inexpensive to produce.

According to the present invention, a surgical device is provided for transperineal biopsy, in particular of the prostate, for a movable arm of a robot as claimed in the attached claims.

BRIEF DESCRIPTION OF THE DRAWINGS

The present invention will now be described with reference to the attached drawings, which illustrate a non-limiting embodiment example thereof, in which.

PREFERRED EMBODIMENTS OF THE INVENTION

Figure 1:
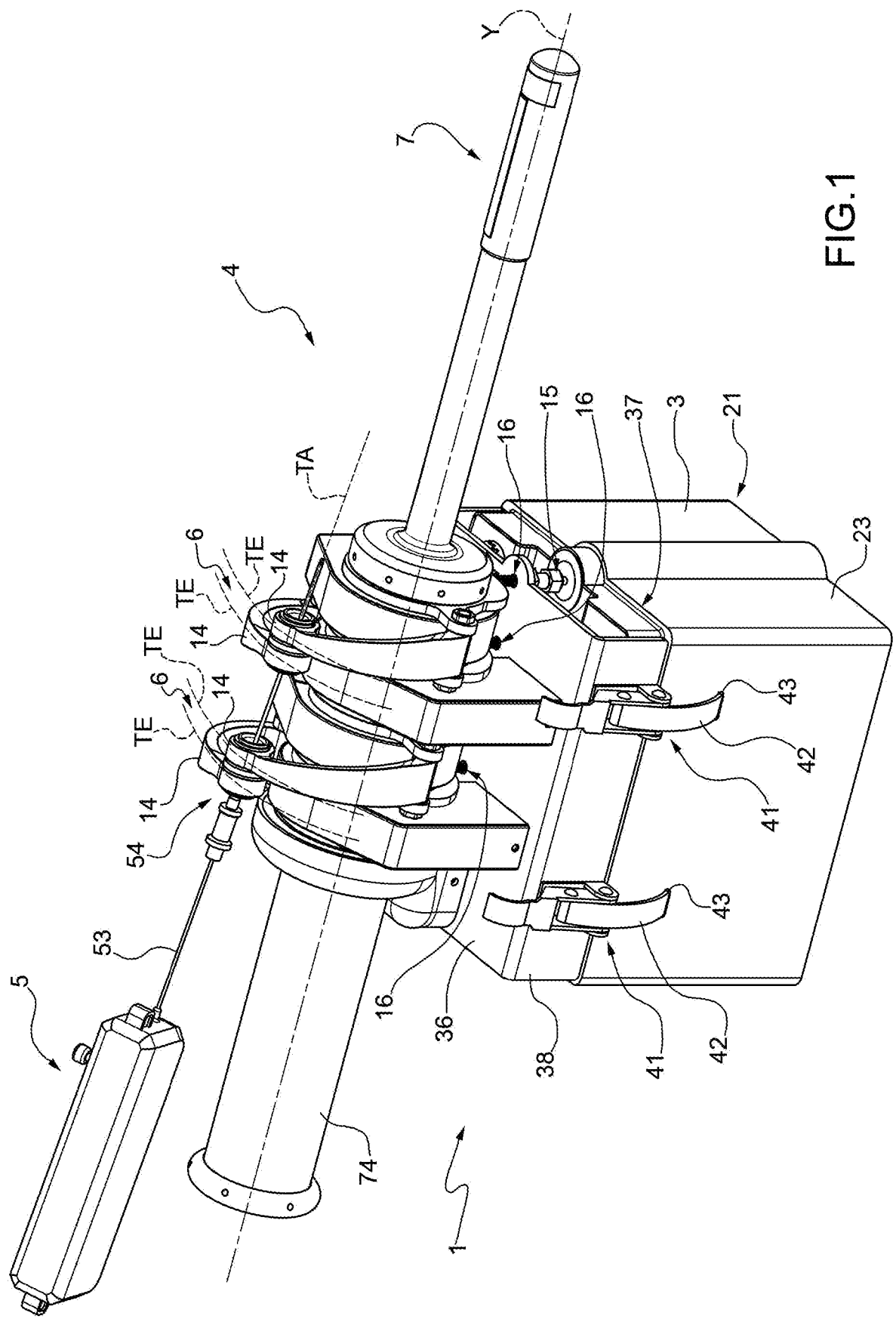
FIG. 1 is a perspective view of a transperineal surgical device produced in accordance with the present invention and coupled with a connection interface.
Figure 2:
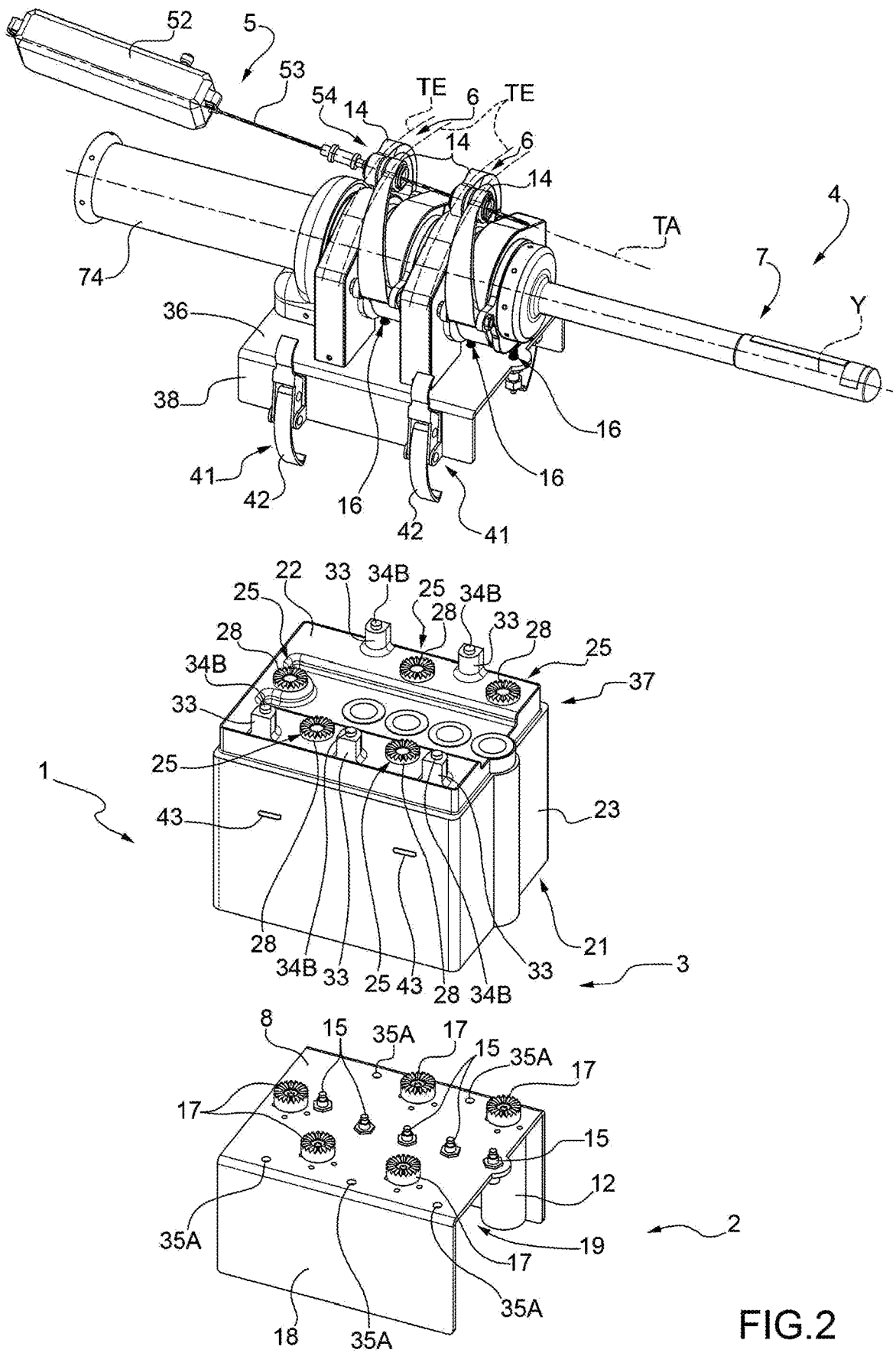
FIG. 2 is a partially exploded view of the transperineal surgical device coupled to the connection interface of FIG. 1.

In FIGS. 1 and 2 the number 1 generically indicates overall a connection interface to couple a surgical device to a movable arm of a commercial type robot (not illustrated), and in particular with a wrist of an anthropomorphic arm of a robot. The connection interface 1 comprises an operating module 2 and a separation module 3, which is configured to be arranged, in use, on the operating module 2. The operating module 2 is illustrated in greater detail in FIGS. 3 and 4; while the separation module 3 is illustrated in greater detail in FIGS. 5 and 6.

Advantageously, the separation module 3 provides a sterile division between the operating module 2 and the surgical device. The separation module can therefore be disposed of after use.

The surgical device is generically indicated by the number 4 and comprises a surgical instrument 5, at least one moving device 6 to move the surgical instrument 5 relative to the movable arm and an intraoperative viewing device 7 which is in particular an ultrasound probe 7. In the example illustrated by FIG. 1, the surgical instrument 5 consists of an automatic extraction unit for soft tissue biopsy.

Figure 4:
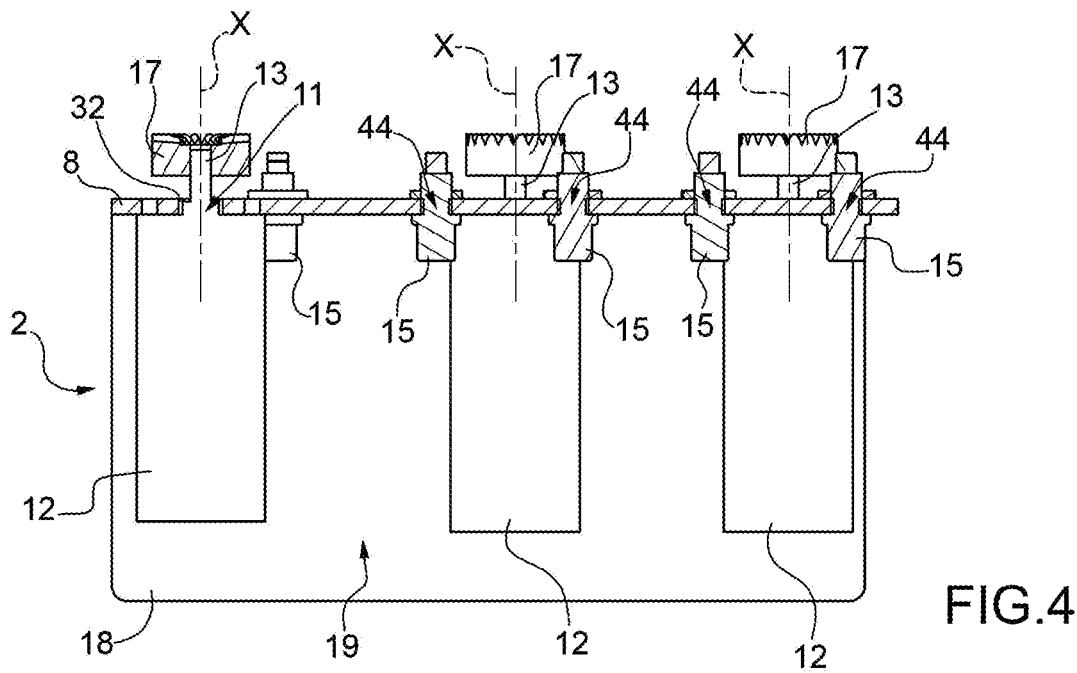
FIG. 4 is a section view of the operating module of FIG. 3 along a line IV-IV.
Figure 3:
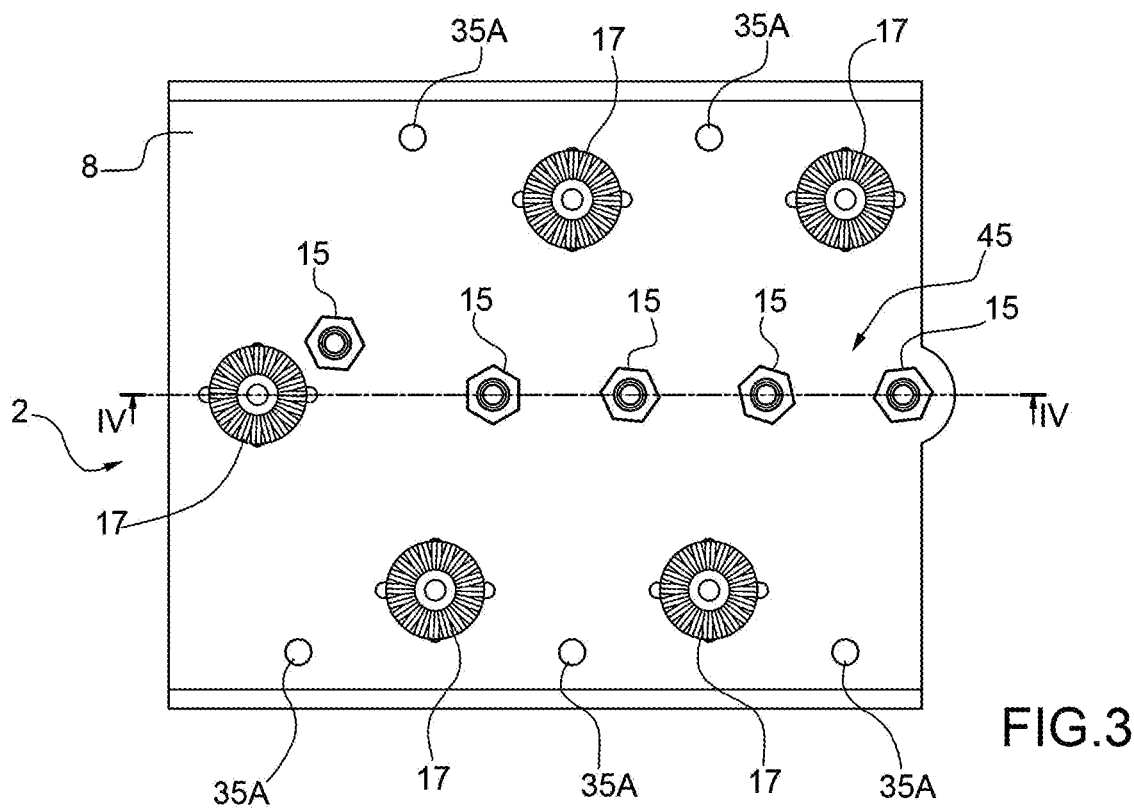
FIG. 3 is a plan view of an operating module of the connection interface of FIGS. 1 and 2.

With reference to FIGS. 3 and 4, the operating module 2 comprises a base wall 8 defined by a plate and having a plurality of through openings 11, each of which has a respective axis X. The operating module 2 further comprises one or more actuators 12, each of which comprises an output shaft 13 mounted through a respective through opening 11, to rotate around the axis X. The axis X is substantially orthogonal to a plane parallel to the base wall 8. Each actuator 12 is configured to generate a certain movement of the surgical device 4 mounted on the connection interface 1. The actuator 12 is not the actuator of the robotic arm, but an actuator 12 of the connection interface 1 and dedicated exclusively to operation of the surgical device 4.

FIGS. 1 and 2 illustrate, merely by way of non-limiting example, the surgical device 4 which specifically comprises two moving devices 6, each of which comprises two guide arms 14 which guide and support the surgical instrument 5 and in particular the needle thereof. As illustrated in the figure, each arm 14 of the moving device 6 and the ultrasound probe 7 are operated individually by a respective actuator 12. Furthermore, the actual positioning of each arm 14 is verified with the aid of a respective position sensor 15 which acquires the information transmitted by means of a cam-tappet system 16, which will be better described below.

In this way it is possible to accurately detect the angular position, and in particular set the angular starting position, i.e. the zero position, of each arm 14, thus consequently controlling the respective actuator 12 taking account of said information.

As illustrated in FIGS. 3 and 4, the output shaft 13 is provided with a motion transmission element 17 which is arranged on the opposite side of the base wall 8 relative to the actuator 12. In other words, the base wall 8 separates the actuator 12 from the motion transmission element 17.

With reference to FIG. 2, according to a possible embodiment, the operating module 2 comprises at least two side walls 18.

Advantageously, the side walls 18 have an extension, along a direction parallel to the axis X, at least equal to the longitudinal dimension of the actuators 12 thus protecting them from accidental side impacts.

According to an alternative embodiment, the side walls 18 have an extension inferior to the longitudinal dimension of the actuators 12. In this case the protection of the actuators 12 would be only partial.

Preferably, the side walls 18 face one another. The base wall 8 and the side walls 18 therefore define a seat 19. The actuator 12 is housed inside the seat 19, while the transmission element 17 is arranged at the opposite side of the base wall 8. In other words, the transmission element 17 is not arranged inside the seat 19.

Figure 6:
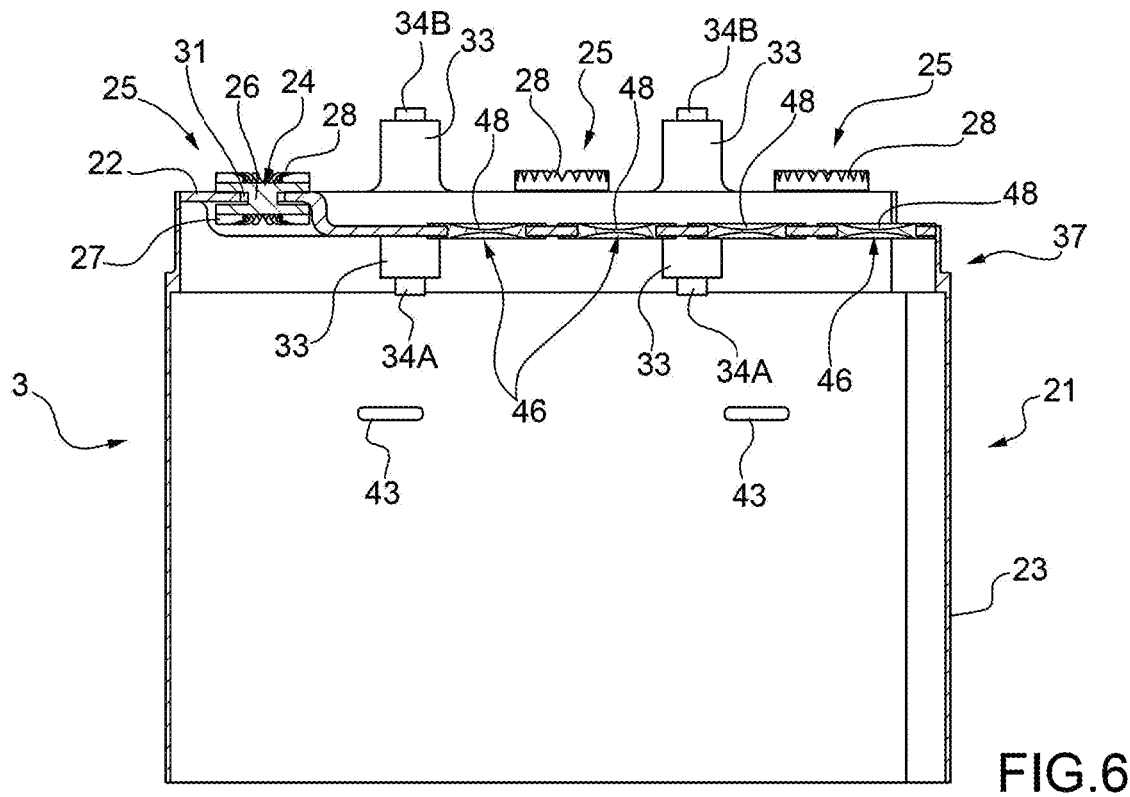
FIG. 6 is a section view of the separation module of FIG. 5 along the line VI-VI.
Figure 5:
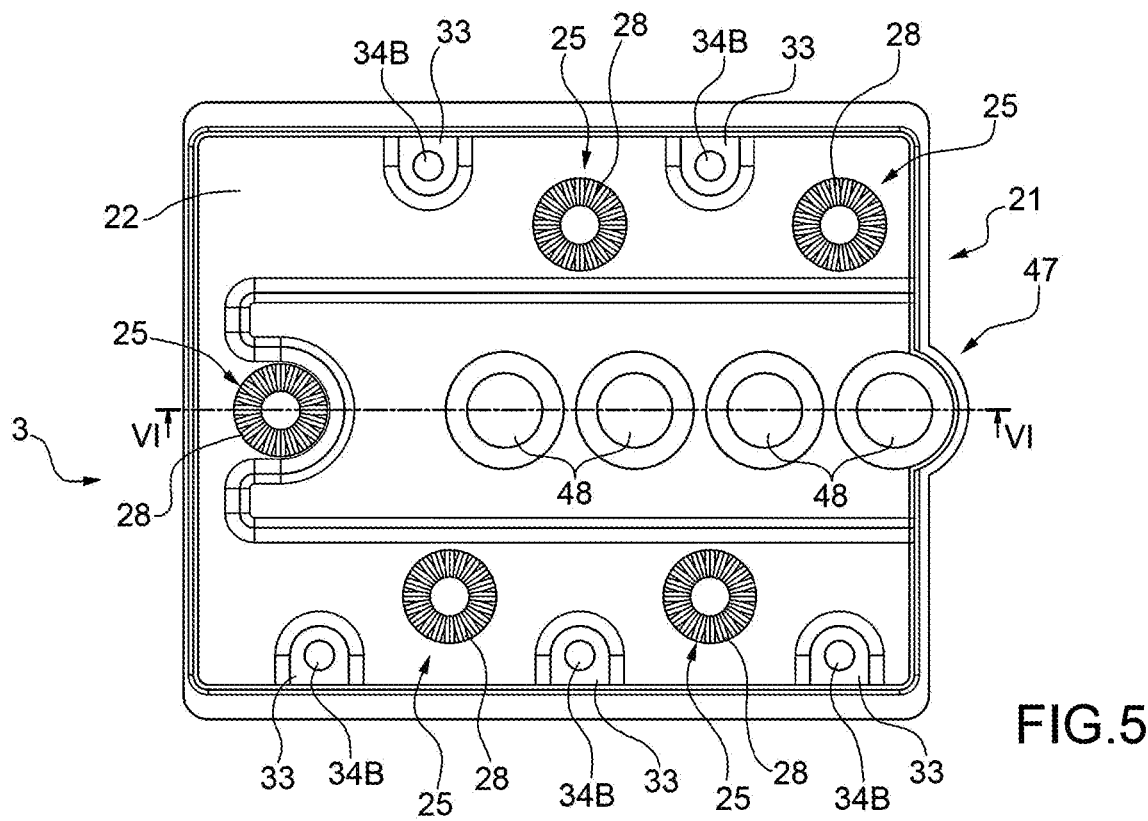
FIG. 5 is a plan view of a separation module of the connection interface of FIGS. 1 and 2.

According to the embodiment illustrated in the figures and in particular in FIGS. 5 and 6, the separation module 3 comprises a cup-shaped body 21, which comprises a base wall 22 and a plurality of side walls 23 so as to be arranged on the operating module 2. In other words, the cup-shaped body 21 is configured to house inside it the operating module 2, in particular to be arranged or fitted on the operating module 2. In particular, the base wall 22 has a plurality of through openings 24 and the cup-shaped body 21 is configured to receive the operating module 2 so that each through opening 24 is coaxial with a respective opening of the through openings 11 of the operating module 2. In other words, each through opening 24 is coaxial with the axis X of a respective through opening 11.

According to what is illustrated in FIGS. 1, 5 and 6, the side walls 23 are rigid and preferably made in one piece with the base wall 22.

According to an alternative embodiment (not illustrated) at least one portion of the side walls 23 is made of a flexible element. The flexible element can comprise for example an element made of plastic such as, for example, cellophane. The flexible element is preferably sterile. The flexible element is connected to the base wall 22. For example the connection between the flexible element and the base wall 22 is provided by means of heat sealing.

The separation module 3 comprises a plurality of transmission members 25, each of which, in use, is designed to transmit the motion from a respective actuator 12 to the surgical device 4. In particular, each transmission member 25 is configured to transmit the motion of the respective actuator 12 to a relative moving device 6 of the surgical device 4.

In particular, each transmission member 25 is arranged through a respective through opening 24 to transmit the motion from a respective motion transmission element 17 to the respective ultrasound probe 7 or the guide arms 14.

According to the preferred embodiment illustrated, each transmission member 25 comprises a shaft 26 provided, at its two ends, with respective motion transmission elements 27 and 28. The shaft 26 is arranged parallel, and in particular coaxial, to the output shaft 13 of the actuator 12, namely to the axis X. The motion transmission element 27 is coupled in a kinematic manner with a respective motion transmission element 17, while the motion transmission element 28 is configured to transmit the motion to the surgical device 4. In particular, the motion transmission element 28 can be coupled in a kinematic manner to a moving device 6 of the surgical device 4, as will be described in detail below.

According to the embodiment illustrated in FIGS. 1-6, each of the motion transmission elements 17, 27 and 28 comprises a gear wheel, and in particular a gear wheel with a face gear mesh. Namely, the gear wheels 17, 27 and 28 relative to a certain actuator 12 have respective teeth arranged along respective planes orthogonal to the axis X.

According to a further and different embodiment (not illustrated) each of the motion transmission elements 17, 27 and 28 comprises any element that can be coupled in a kinematic manner, preferably frontally, for example a joint or a clutch.

According to a further and different embodiment (not illustrated) the elements 17 and 27 are of different type from the transmission element 28 and the respective transmission element of the surgical device 4. In other words, the motion transmission elements 17 or 27 and the element 28 or the respective transmission element of the surgical device 4, which therefore do not couple in a kinematic manner with one another, can be of different type from one another.

Obviously in order to couple in a kinematic manner the motion transmission element 17 with the motion transmission element 27 and similarly the transmission element 28 with the respective motion transmission element of the surgical device 4, they must necessarily be of the same type so as to allow the coupling.

The second base wall 22 separates the motion transmission element 27 from the motion transmission element 28. In other words, the motion transmission element 27 and the motion transmission element 28 are arranged on opposite sides of the base wall 22.

According to what is illustrated in FIG. 6, to further guarantee that no type of material and/or fluid can pass from the separation module 3 to the surgical device 4, and vice versa, the separation module 3 comprises one or more seal elements 31, each of which is arranged at a respective through opening 24.

Alternatively or additionally, as illustrated in FIG. 4, the operating module 2 comprises one or more seal elements 32, each of which is arranged at a respective through opening 11. According to a possible embodiment, the separation module 3 comprises support elements 33 which project from the base wall 22 of the cup-shaped body 21 to support the surgical device 4. In particular, the support elements 33 are arranged at the side edges of the base wall 22 of the cup-shaped body 21. The support elements 33 consist of protrusions provided at the base wall 22. Each of the support elements 33 have, at a free end of their own, a pin 34A or 34B which is configured to engage an opening 35A or 35B. The opening 35A or 35B is substantially a centring hole of the respective pin 34A or 34B.

Advantageously, the support elements 33 are arranged on at least one side of the base wall 22 of the separation module 3. Preferably, the support elements 33 are arranged on both sides of the base wall 22, as illustrated in FIG. 6. Each of the support elements 33 arranged on the inner side of the base wall 22, namely inside the cup-shaped body 21, has the pin 34A configured to engage the respective through or blind opening 35A provided in the operating module 2. Preferably, the opening 35A is blind, to prevent material and/or fluid from being able to pass from the operating module 2 to the surgical device 4, and vice versa.

Each of the support elements 33 arranged on the outer side of the base wall 22 has the pin 34B configured to engage a respective through or blind opening 35B (not illustrated) provided in a base element 36 of the surgical device 4.

Preferably, the opening 35B is blind, to prevent material and/or fluid from being able to pass from the separation module 3 to the surgical device 4, and vice versa.

According to a further embodiment not illustrated, the support elements 33 are arranged on the base element 36 of the surgical device 4. According to this embodiment, the opening 35B is arranged at the base wall 22. The opening 35B is preferably blind. This embodiment allows improved cleaning of the surgical device 4.

According to a possible embodiment, the separation module 3 comprises, at the side walls 23, an abutment edge 37. The abutment edge 37 is engaged, in use, by one or more side portions 38 of the base element 19 of the surgical device 4. To guarantee correct fixing of the surgical device 4 with the connection interface 1, at least one fixing means 41 is provided, illustrated in FIGS. 1 and 2.

According to the embodiment illustrated in FIGS. 1 and 2, the fixing means 41 is arranged on the base element 36 of the surgical device 4, and in particular on at least one of the side portions 38, to connect it to the separation module 3 or to the operating module 2.

The fixing means 41 comprises a spring lever. In particular, the spring lever comprises a lever 42 which is hinged on a side portion 38 of the surgical device 4. The lever 42 is configured to move between a closed position and an open position. In the closed position a free end of the lever 42 couples with an abutment element 43 obtained on a relative side wall 23 of the cup-shaped body 21 (for example if the side walls 23 are rigid) or on a relative side wall 18 of the operating module 2 (for example if the side walls 23 comprise a flexible element). In this way it is possible to block the surgical device 4 on the connection interface 1. In the open position the free end of the lever 42 uncouples from the abutment element 43 so as to allow the release of the surgical device 4 from the connection interface 1.

According to an alternative embodiment (not illustrated), the fixing means 41 is arranged on at least two side walls 23 of the cup-shaped body 21 (for example if the side walls 23 are rigid), preferably facing one another, or on two side walls 18, preferably facing each other, of the operating module 2 (for example if the side walls 23 comprise the flexible element). In other words, the respective lever 42 is hinged on the side wall 23 of the cup-shaped body 21 (if the side walls 23 are rigid) or on the side wall 18 of the operating module 2 (if the side walls 23 comprise a flexible element). The respective abutment element 43 is obtained in one of the side portions 38 of the base element 38 of the surgical device 4.

In the preferred embodiment the side walls 23 comprise the flexible element and the surgical device 4 is connected to the operating module 2, maintaining the separation module 3 interposed between them. Therefore, according to this embodiment the respective abutment element 43 is obtained at the side wall 18 of the operating module 2.

Advantageously, the fixing means 41 comprises a sensor (not illustrated) designed to detect correct closing of the fixing means 41 and in particular of the lever 42. If the fixing means 41 is not closed correctly or inadvertently opens during use, the sensor sends a signal to warn the operator of the incorrect closing of the fixing means 41.

With reference to FIGS. 3 and 4, the base wall 8 further comprises at least one or more through openings 44 configured to house at least partially the position sensors 15 as illustrated in FIG. 4.

Preferably, the through openings 44 are provided at a centre line 45 of the base wall 8. By centre line 45 we mean the central zone of the base wall 8 along the longitudinal extension thereof. In particular, the centre line 45 is arranged substantially at the section line IV-IV of FIG. 3. There are preferably more than two through openings 44.

With reference to FIGS. 5 and 6, the base wall 22 comprises one or more through openings 46. Preferably, the through openings 46 are made at a centre line 47 of the base wall 22. By centre line 47 we mean the central zone of the base wall 22 along the longitudinal extension thereof.

In particular, the centre line 47 is arranged substantially at the section line VI-VI of FIG. 5. There are preferably more than two through openings 46. The cup-shaped body 21 is configured to receive the operating module 2 so that each through opening 44 is aligned, namely coaxial, with a respective through opening 46.

Advantageously, at each through opening 46 a seal element 48 is arranged, consisting for example of a membrane. The seal element 48 prevents any material and/or fluid from passing from the operating module 2 to the surgical device 4, and vice versa. Furthermore, the seal element 48, being flexible, allows transmission of the movement of the cam-tappet system 16 to the position sensor 15 in an accurate manner while maintaining a separation between the elements, in particular the tappet and the position sensor 15, which interact.

As illustrated in FIGS. 5 and 6, the base wall 22 has a lowered zone at the centre line 47. At the lowered zone the base wall 22 has a thickness preferably equal to other zones of the base wall 22. In other words, the wall 22 has a constant thickness along the entire extension.

The connection interface 1 thus obtained is adapted to be carried by, and connected to, the movable arm of a robot. In particular, the base wall 8 and the side walls 18 of the operating module 2 form a frame, which can be carried by the movable arm of a robot.

According to a possible alternative, between the connection interface 1 and the movable arm of the robot a connection body is interposed (not illustrated). In said case the connection body acts as an adapter for connection of the connection interface 1 and the movable arm of the robot.

The actuators 12 can be connected to a control unit (not illustrated) of the robot by means of electric wires (not illustrated) carried by the movable arm and can be controlled independently of one other by the control unit according to the specific use of the surgical device 4. The control unit can belong to the robot or can be an external control unit.

In use, the separation module 3 and the operating module 2 overlap each other so that the operating module 2 is arranged in the cup-shaped body 21 of the separation module 3. During coupling of the two modules 2 and 3, the elements 17 and 27 interact with each other so as to guarantee transmission of the motion. The transmission is preferably synchronous. The surgical device 4 is arranged on the connection interface 1 and is fixed to it by means of the fixing means 41.

The surgical device 4 is a device for transperineal biopsy and comprises the ultrasound probe 7, the surgical instrument 5 and the moving device 6 of the surgical instrument 5.

The ultrasound probe 7 is configured to be inserted, in use, in a natural orifice (for example the rectum) of the patient.

The ultrasound probe 7 is mounted to rotate around an axis Y (which is transversal, in particular orthogonal to the axis X) and is rotated by motion transmission members 51 operated by the respective actuator 12.

The surgical instrument 5 comprises a sampling unit 52 which is arranged above the ultrasound probe 7. The sampling unit 52 is designed to perform the biopsy. Namely, the sampling unit 52 is provided with a needle 53 which removes material, soft tissue or other from the patient. Preferably, the sampling unit 52 is a so-called biopsy gun, a guillotine biopsy device, or any device adapted to remove material.

As illustrated in FIGS. 1 and 2, the needle 53 is movable along a trajectory TA to arrange it in the patient at a given and precise position spaced from the natural orifice of said patient. The needle 53 is guided and supported by the arms 14 of the moving device 6, as explained in further detail below. Preferably, the moving device 6 comprises at least a pair of arms 14, in which each arm 14 is arranged on an opposite side around the axis Y. In particular, the two arms 14 are arranged in succession around the axis Y, but on two different and opposite sides.

Advantageously, the moving device 6 comprises two pairs of arms 14 arranged in succession around the axis Y which move respectively along the trajectory TE.

Each arm 14 is operated by an actuator 12 of its own and is mounted mobile, preferably oscillatable around the axis Y, along the trajectory TE. The arms 14, moving on the trajectory TE, guide and support the needle 53.

As can be seen from FIGS. 1 and 2, the arms 14 guide and support the needle 39 along the trajectory TA at a free end 54 thereof. The free end 54 comprises a guide portion which supports and guides the needle 39 so that it covers the trajectory TA. The trajectory TA covered by the needle 53 is different from the trajectory TE covered by each arm 14.

Figure 7:
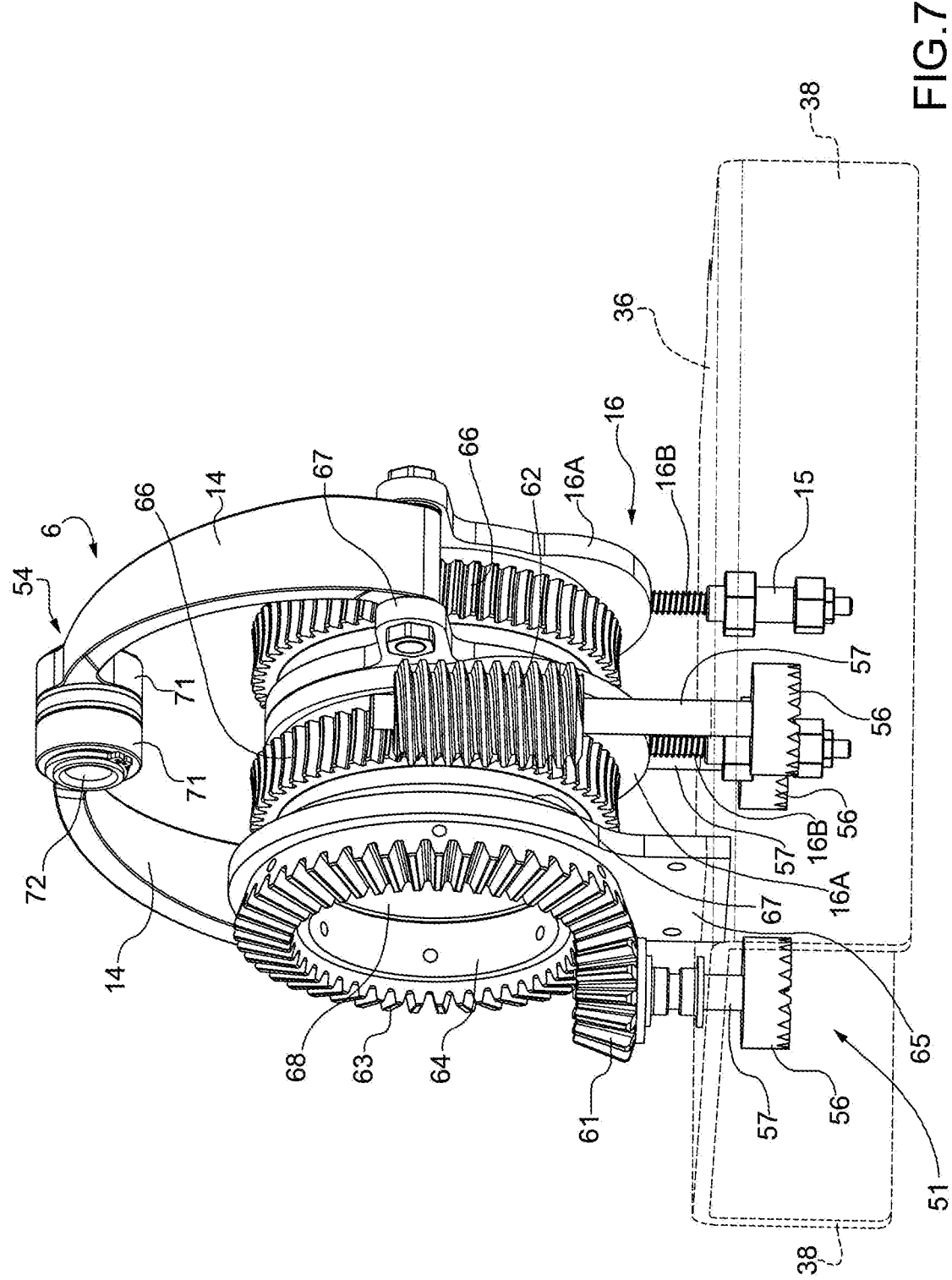
FIG. 7 is a perspective and enlarged view of a portion of the transperineal surgical device of FIGS. 1 and 2, from which parts have been removed for greater clarity.

In FIG. 7 a possible embodiment is illustrated of the surgical device 4 comprising members 51 for transmission of the motion from the connection interface 1 to the surgical device 4 for transperineal biopsy. The motion transmission members 51 comprise the motion transmission elements 56. The motion is transmitted from the separation module 3 to the surgical device 4 for transperineal biopsy by means of the kinematic coupling between the motion transmission element 28 of the separation module 3 and the respective motion transmission element 56 of the surgical device 4 for transperineal biopsy. In particular, the motion is transmitted by a plurality of motion transmission elements 28 which are coupled in a kinematic manner with the respective motion transmission element 56. Each motion transmission element 56 is mounted on a respective shaft 57. The motion transmission elements 56 are arranged between the motion transmission members 25 and the motion transmission elements 61, 62.

According to the embodiment illustrated in FIG. 7, the motion transmission element 56 comprises gear wheels with a face gear mesh, which rotate around an axis preferably parallel to the axis X, namely the gear wheels 56 have respective teeth arranged along respective planes orthogonal to the axis around which they rotate.

According to a further and different embodiment (not illustrated) the motion transmission elements 56 comprise any element that can be coupled in a kinematic manner preferably frontally such as, for example, a joint or a clutch. Obviously in order for the motion transmission element 56 to couple in a kinematic manner with the motion transmission element 28 of the connection interface 1, they must necessarily be of the same type, in order to enable the coupling.

As can be seen from FIG. 7, the shaft 57 is configured to be arranged across through openings 58 provided at the base element 36. On the opposite end of the shaft 57 the motion transmission element 61 or 62 is arranged, according to whether the ultrasound probe 7 or the arm 14 of the moving device 6 has to be operated. In other words, the shaft 57 that operates the ultrasound probe 7 comprises at its own end the motion transmission element 61, while the shaft 57 that operates the arm 14 of the moving device 6 comprises at its own end the motion transmission element 62.

The motion transmission element 61 is configured to couple in a kinematic manner with a motion transmission element 63 which is integrally connected to the ultrasound probe 7, to transmit the motion from a respective transmission member 25 to the ultrasound probe 7 to rotate it. In particular, the ultrasound probe 7 and the motion transmission element 63 are arranged, namely mounted, integral with the hollow shaft 64. The motion transmission element 63 is arranged around the hollow shaft 64, whereas the ultrasound probe 7 is arranged inside the hollow shaft 64. The hollow shaft 64 is supported, preferably at an end of its own, by at least one support bracket 65 fixed to the base element 36.

The motion transmission element 62 is configured to couple in a kinematic manner with a motion transmission element 66 which is connected integrally to the cam-tappet system 16, to transmit the motion from a respective transmission member 25 to the respective arm 14, thus causing the respective arm 14 to move along the trajectory TE. In particular, the motion transmission element 66 rotates the cam 16A to which the respective arm 14 is connected. The connection between the cam 16A and the arm 14 can be provided by means of a threaded connection.

In particular each arm 14 is carried on one side by its own cam 16A and on the opposite side by a support element 67. The cam 16A, by moving, causes the tappet 16B to translate upwards or downwards, thus transmitting the angular position of the cam 16A to the position sensors 15. In this way it is possible to accurately detect the angular position, and in particular set the starting angular position, namely the zero, of each arm 14, thus consequently commanding the actuator 12 taking account of said information.

The elements 66, 67 and 16A associated with each arm 14 are arranged on a hollow shaft 68 coaxial with the axis Y.

The motion transmission element 66, the cam 16A and the support 67 of each arm 14 are arranged on the hollow shaft 68, so that they can freely rotate on it. The shaft 68 is hollow so that the ultrasound probe 7 can be arranged inside it. The ultrasound probe 7 is not connected to the hollow shaft 68 and therefore does not influence the rotation thereof. There is therefore no kinematic interaction between the ultrasound probe 7 and each arm 14. The hollow shaft 68 is supported at its own end by support brackets (not illustrated). The support brackets of the hollow shaft 68 are substantially similar to the support bracket 65 of the hollow shaft 64.

In accordance with the embodiment illustrated in FIG. 7, the motion transmission elements 61 and 63 respectively comprise a gear wheel, preferably a bevel gear wheel. The gear wheel 61 rotates around the vertical axis parallel to the axis X. In particular, when the surgical device 4 for transperineal biopsy is connected to the connection interface 1, the vertical axis is coaxial with the axis X. The gear wheel 63, on the other hand, rotates around the axis Y. According to this embodiment, the motion transmission elements 62 and 66 respectively comprise a worm screw and a cylindrical wheel. The worm screw 62 rotates around the vertical axis parallel to the axis X. In particular, when the surgical device 4 for transperineal biopsy is connected to the connection interface 1, the vertical axis is coaxial with the axis X. The gear wheel 66, on the other hand, rotates around the axis Y.

Therefore, the kinematic chain that transmits the motion from the actuator 12 to the ultrasound probe 7 comprises the motion transmission elements 17, 27, 28, 56, 61 and 63.

The kinematic chain that transmits the motion from the actuator 12 to the respective arm 14 comprises the motion transmission elements 17, 27, 28, 56, 62 and 66.

As can be seen from FIGS. 1, 2 and 7, the arms 14 have mainly a longitudinal extension and are arranged with their own extension substantially transversal to the axis Y. Preferably, the arms 14 are shaped like a curved line. In particular, as illustrated, the arms 14 have a substantially rectangular cross-section decreasing towards the free end, namely the arm 14 has a cross-section with larger dimension at the end connected to the cam 16A and to the support 67 than the free end 54. At the free end a guide portion 71 is arranged. The guide portion 71 comprises a cylindrical section arranged substantially tangent to the cross-section. The guide portion 71 comprises a ball joint defining inside it a through opening 72 through which the needle 53 is arranged. The through openings 72 of two adjacent arms that cooperate are arranged facing each other, preferably they are substantially coaxial. As can be clearly seen from the figures, the through opening 72 is substantially transversal relative to the longitudinal extension of the arm 14. The needle 53 is then oriented and/or directed along the trajectory TA via the movement along the trajectory TE of each arm 14.

According to an alternative embodiment, not illustrated, the guide portion 71 of each arm 14 has a "V", "U" or "C" shaped seat, has a substantially transversal longitudinal extension and is open laterally. The seats of each arm 14 of the same pair of arms 14 are substantially coaxial to each other.

Each moving device 6 comprises a pair of arms 14. As already previously described, the two arms 14 are respectively arranged on opposite sides to each other around the axis Y. Therefore, each arm 14 moves along its own trajectory TE. The trajectories TE of the pair of arms 14 are substantially parallel to each other and are traveled in the opposite direction. In other words, since the through openings 72 or the seats have to remain facing one another, if an arm 14 moves closer to or farther away from the other arm 14, the latter must follow it so as to guarantee the guide and support of the needle 53. The arms 14 of the same pair move preferably simultaneously, namely in a synchronous manner, but in an opposite direction. The trajectory TE is at least partially curved, thus varying the inclination and/or the trajectory TA of the needle 53. In this way it is possible to carry out fine adjustments of the radial movement and/or of the inclination of the needle 53 along the trajectory TA.

Advantageously, the surgical device 4 for transperineal biopsy comprises several pairs of arms 14.

In this way it is possible to act on the needle 53 at several points, increasing the accuracy with which the trajectory TA is covered by the needle 53.

According to a possible embodiment, the device 34 comprises a perforated grid (not illustrated) which acts as a viewfinder for the needle 53. The perforated grid is optional. The perforated grid has a plurality of through openings which are distributed in an orderly equidistant manner. The perforated grid is optional.

As illustrated in FIGS. 1 and 2 the surgical device 4 comprises a grip 74.

In use, the ultrasound probe 7 is inserted inside the natural orifice of the patient and the actuators 12 which are connected to the control unit (not illustrated) are controlled by it so as to move the ultrasound probe 7 and each arm 14 in the desired manner. By moving the ultrasound probe 7 it is possible to detect the angular position of said ultrasound probe 7 and it is possible to instantly see the organs and surrounding tissues. By moving the arms 14 along their trajectory TE it is possible to guide the needle 53 along the trajectory TA. The trajectory TA is established taking account of the image mapping, for example radiographic or obtained by means of magnetic resonance, obtained in the pre-operative phase and comparing them with the current images, called intraoperative, obtained by means of the ultrasound probe 7. In this way it is possible to establish the biopsy target also taking account of the deformation of the organ due to the contact with the ultrasound probe 7. It is therefore possible to correct the trajectory TA according to the deformation of the organ in contact with the ultrasound probe 7.

The surgical device 4 for transperineal biopsy described so far has a plurality of advantages.

The main advantage is that it can be mounted on any commercial robot via the connection interface 1. Therefore, the surgical device 4 is cheaper than any other device made exclusively for a precise and given model of medical robot.

Through the arms 14 it is possible to obtain instant correction of the trajectory TA of the needle 53 according to the angular position of the ultrasound probe 7. In fact, by acting on the trajectory TE of each arm 14 it is possible to influence the trajectory TA of the needle 53.

Furthermore, the surgical device 4 has the advantage that the needle 53 is not inserted manually into the patient, but by means of the moving device 6 which orients and inclines the needle 53 according to the intraoperative images acquired by the ultrasound probe 7. The surgical device 4 for transperineal biopsy in fact allows an instant correlation to be made between the preoperative images and the intraoperative images, also taking account of the deformation of the organ in contact with the ultrasound probe 7.

The invention claimed is:

1. A device for transperineal biopsy, in particular of the prostate, for a movable arm of a robot, comprising:
   an ultrasound probe being mounted rotatable around a first longitudinal axis and being configured to be inserted, in use, into a natural orifice of a patient;
   a surgical instrument being provided with a needle, which is movable along a first trajectory and configured to be inserted, in use, spaced apart from the natural orifice;
   a moving device of the surgical instrument comprising at least one pair of guide arms facing one another and arranged around said first longitudinal axis so as to move, preferably oscillate, around the first longitudinal axis along a second trajectory, which is different from the first trajectory, in order to guide and support the needle at a free end of each guide arm; and
   a connection interface designed to be connected to said movable arm of the robot and comprising an operating module, which comprises a plurality of actuators each to move a respective said ultrasound probe or said guide arms, and a separation module, which comprises a cup-shaped body arranged on the operating module;
   the operating module comprising a first base wall having a plurality of first through openings having respective substantially crosswise second axes, in particular orthogonal, to the first longitudinal axis; each actuator comprising an output shaft, which is provided with a first motion transmission element and is mounted through a respective first through opening with the first motion transmission element arranged on an opposite side of the first base wall with respect to the actuator; the cup-shaped body comprising a second base wall having a plurality of second through openings, each of which is coaxial with a respective first through opening and the separation module comprising a plurality of transmission members, each of which is arranged through a respective second through opening to transmit the motion from a respective first motion transmission element to a respective said ultrasound probe or said guide arms;

wherein the device for transperineal biopsy comprises fixing means to block a base element configured to engage an abutment element obtained on a wall of the separation module or of the operating module to block the base element to the respective separation module or operating module.

2. The device according to claim 1, comprising:

a second motion transmission element rotatable around the respective second axis and a third motion transmission element rotatable around the first longitudinal axis and coupled in a kinematic manner to each other to transmit the motion from a respective transmission member to said ultrasound probe; and fourth motion transmission elements rotatable around the respective second axis and fifth motion transmission elements rotatable around the first longitudinal axis and coupled in a kinematic manner to each other to transmit the motion from a respective transmission member to a respective guide arm.

3. The device according to claim 2, comprising sixth motion transmission elements arranged respectively on opposite ends of first shafts on which a respective second motion transmission element or fourth motion transmission element is arranged; said sixth motion transmission elements being arranged between the motion transmission members and said second or fourth motion transmission elements.

4. The device according to claim 2, wherein the second motion transmission element comprises a first gear wheel, preferably a bevel gear wheel;

the third motion transmission element comprises a second gear wheel, preferably a bevel gear wheel, mounted on a first hollow shaft coaxial with the first longitudinal axis and inside which the ultrasound probe is integrally mounted;

the fourth motion transmission elements comprising a third gear wheel, preferably a worm screw;

the fifth motion transmission elements comprising a fourth gear wheel mounted on a second hollow shaft to which a cam is integrally mounted which causes the movement of the respective guide arm connected to it.

5. The device according to claim 3, wherein the first motion transmission elements and the sixth motion transmission elements comprise a gear wheel, preferably a gear wheel with a face gear mesh, a joint or a clutch; and the transmission members comprising two gear wheels, preferably with a face gear mesh, two joints or two clutches mounted on opposite ends of a second shaft.

6. The device according to claim 4, wherein the cam acting on a tappet transmits the angular position of the cam and therefore of the guide arm to a position sensor.

7. The device according to claim 1, the guide arms having a cross-section decreasing towards the free end and being arranged in succession along the first longitudinal axis and with longitudinal extension crosswise to the first longitudinal axis.

8. The device according to claim 1, comprising several pairs of guide arms; each pair being arranged in succession along the first longitudinal axis.

9. The device according to claim 1, wherein each guide arm is provided at the free end with a third through opening or a seat, through which the needle extends; and the third through openings or the seats of the guide arms of the pair facing each other, preferably coaxial.

10. The device according to claim 1, wherein the second trajectory covered by each guide arm is at least partially curved.

11. The device according to claim 3, comprising a base element provided with a plurality of third through openings through which the first shafts are arranged.

12. The device according to claim 1, the separation module comprising support elements, which protrude from the second base wall of the cup-shaped body, in particular at side edges of the second base wall.

13. The device according to claim 1, said first base wall having at least a third through opening made at a first centre line of the first base wall and the second base wall having at least a fourth through opening, made at a second centre line of the second base wall; said cup-shaped body being configured to be arranged on the operating module so that the fourth through opening is aligned with the third through opening.

14. The device according to claim 6, wherein said first base wall having at least a third through opening made at a first centre line of the first base wall and the second base wall having at least a fourth through opening, made at a second centre line of the second base wall; said cup-shaped body being configured to be arranged on the operating module so that the fourth through opening is aligned with the third through opening; the position sensor is arranged in the third opening; a seal element being arranged in the fourth opening; and the cam and the tappet being arranged respectively on opposite sides of the seal element.

* * * * *